(12) United States Patent
Bono et al.

(10) Patent No.: US 10,835,263 B2
(45) Date of Patent: Nov. 17, 2020

(54) ROTARY OSCILLATING SURGICAL TOOL

(71) Applicant: Peter L. Bono, Bingham Farms, MI (US)

(72) Inventors: Peter L. Bono, Bingham Farms, MI (US); James D. Lark, West Bloomfield, MI (US); John S. Scales, Ann Arbor, MI (US)

(73) Assignee: Peter L. Bono, Bingham Farms, MI (US)

(*) Notice: Subject to any disclaimer, the term of this patent is extended or adjusted under 35 U.S.C. 154(b) by 443 days.

(21) Appl. No.: 15/814,891

(22) Filed: Nov. 16, 2017

(65) Prior Publication Data

US 2018/0140307 A1 May 24, 2018

Related U.S. Application Data

(60) Provisional application No. 62/423,624, filed on Nov. 17, 2016.

(51) Int. Cl.
*A61B 17/16* (2006.01)
*A61B 17/32* (2006.01)
*A61B 17/00* (2006.01)

(52) U.S. Cl.
CPC ...... *A61B 17/1624* (2013.01); *A61B 17/1626* (2013.01); *A61B 17/1628* (2013.01); *A61B 17/162* (2013.01); *A61B 17/1622* (2013.01); *A61B 17/1671* (2013.01); *A61B 17/32002* (2013.01); *A61B 2017/00398* (2013.01); *A61B 2017/00734* (2013.01); *A61B 2017/320028* (2013.01)

(58) Field of Classification Search
CPC .............. A61B 17/162; A61B 17/1622; A61B 17/1624; A61B 17/1626; A61B 17/1628
See application file for complete search history.

(56) References Cited

U.S. PATENT DOCUMENTS

| | | |
|---|---|---|
| 1,154,159 A | 9/1915 | Ashworth |
| 2,557,429 A | 6/1951 | Hawley |
| 2,831,295 A | 4/1958 | Weiss |
| 3,091,060 A | 5/1963 | Giegerich et al. |
| 3,554,197 A | 1/1971 | Dobbie |
| 3,577,579 A | 5/1971 | Duve et al. |
| 4,007,528 A | 2/1977 | Shea et al. |
| 4,008,720 A | 2/1977 | Brinckmann et al. |
| 4,081,704 A | 3/1978 | Vassos et al. |
| RE29,736 E | 8/1978 | Shea et al. |
| D248,967 S | 8/1978 | Shea et al. |
| 4,111,208 A | 9/1978 | Leuenberger |
| 4,596,243 A | 6/1986 | Bray |
| 4,620,539 A | 11/1986 | Andrews et al. |

(Continued)

FOREIGN PATENT DOCUMENTS

| | | |
|---|---|---|
| AR | 42807 | 7/2005 |
| AT | 370608 | 4/1983 |

(Continued)

*Primary Examiner* — Anu Ramana
(74) *Attorney, Agent, or Firm* — McHale & Slavin, P.A.

(57) ABSTRACT

A surgical tool with a housing, and a cutter support shaft operably connected to a motor to effect rotation of the shaft with a drive transmission configured between the motor and the shaft to effect oscillating rotary movement of the shaft and cutter is disclosed.

10 Claims, 6 Drawing Sheets

(56) References Cited

U.S. PATENT DOCUMENTS

| | | | |
|---|---|---|---|
| 4,828,052 A | 5/1989 | Duran et al. |
| 4,932,935 A | 6/1990 | Swartz |
| 5,092,875 A | 3/1992 | McLees |
| 5,522,829 A | 6/1996 | Michalos |
| 5,733,119 A | 3/1998 | Carr |
| 5,843,110 A | 12/1998 | Dross et al. |
| 6,021,538 A | 2/2000 | Kressner et al. |
| 6,110,174 A | 8/2000 | Nichter |
| 6,635,067 B2 | 10/2003 | Norman |
| 6,689,087 B2 | 2/2004 | Pal et al. |
| 6,716,215 B1 | 4/2004 | David et al. |
| 6,721,986 B2 | 4/2004 | Zhaun |
| 6,966,912 B2 | 11/2005 | Michelson |
| 7,160,304 B2 | 1/2007 | Michelson |
| 7,922,720 B2 | 4/2011 | May et al. |
| 8,029,523 B2 | 10/2011 | Wallis et al. |
| 8,038,630 B2 | 10/2011 | Pal et al. |
| 8,465,491 B2 | 6/2013 | Yedlicka et al. |
| 8,657,821 B2 | 2/2014 | Palermo |
| 8,728,085 B2 | 5/2014 | Marsh et al. |
| 8,828,001 B2 | 9/2014 | Stearns et al. |
| 8,943,634 B2 | 2/2015 | Sokol et al. |
| 9,295,815 B2 * | 3/2016 | Stevens ............ A61M 25/09041 |
| 2004/0050603 A1 | 3/2004 | Jaeger |
| 2004/0147934 A1 | 7/2004 | Kiester |
| 2005/0283175 A1 | 12/2005 | Tanner et al. |
| 2006/0229624 A1 | 10/2006 | May et al. |
| 2006/0235305 A1 | 10/2006 | Cotter et al. |
| 2006/0235306 A1 | 10/2006 | Cotter et al. |
| 2007/0282344 A1 | 12/2007 | Yedlicka et al. |
| 2007/0282345 A1 | 12/2007 | Yedlicka et al. |
| 2008/0027449 A1 | 1/2008 | Gundlapalli et al. |
| 2008/0061784 A1 | 3/2008 | Pal et al. |
| 2008/0108010 A1 | 5/2008 | Wang |
| 2008/0213899 A1 | 9/2008 | Olgac |
| 2010/0145343 A1 | 6/2010 | Johnson et al. |
| 2010/0165793 A1 | 7/2010 | Haug |
| 2010/0249786 A1 | 9/2010 | Schmieding et al. |
| 2011/0015635 A1 | 1/2011 | Aryan |
| 2011/0066155 A1 * | 3/2011 | Del Rio ............ A61B 17/1659 |
| | | 606/85 |
| 2011/0196404 A1 | 8/2011 | Dietz et al. |
| 2011/0230886 A1 | 9/2011 | Gustilo et al. |
| 2011/0295270 A1 | 12/2011 | Giordano et al. |
| 2011/0306873 A1 | 12/2011 | Shenai et al. |
| 2012/0186372 A1 | 7/2012 | Smith et al. |
| 2012/0211546 A1 | 8/2012 | Shelton, IV |
| 2013/0178856 A1 | 7/2013 | Ye et al. |
| 2013/0206441 A1 | 8/2013 | Roser et al. |
| 2013/0245629 A1 | 9/2013 | Xie |
| 2013/0304069 A1 | 11/2013 | Bono et al. |
| 2014/0100574 A1 | 4/2014 | Bono et al. |
| 2014/0222003 A1 | 8/2014 | Herndon et al. |
| 2014/0262408 A1 | 9/2014 | Woodward |
| 2014/0350571 A1 | 11/2014 | Maillet et al. |
| 2015/0119916 A1 | 4/2015 | Dietz et al. |
| 2015/0133960 A1 | 5/2015 | Lohmeier et al. |

FOREIGN PATENT DOCUMENTS

| | | |
|---|---|---|
| AU | 2003200831 | 11/2006 |
| AU | 2011215901 | 8/2012 |
| BE | 861446 | 3/1978 |
| CA | 1112970 | 11/1981 |
| CA | 2513071 | 7/2004 |
| CA | 2788918 | 8/2011 |
| CH | 610753 | 5/1979 |
| CL | 252004 | 3/2005 |
| CN | 102781349 | 11/2012 |
| DE | 2730227 | 6/1978 |
| DK | 570977 | 6/1978 |
| EP | 0148304 | 7/1985 |
| EP | 0261260 | 3/1988 |
| EP | 1571581 | 9/2005 |
| EP | 1581374 | 2/2006 |
| EP | 1041918 | 3/2006 |
| EP | 1690649 | 8/2006 |
| EP | 2533703 | 12/2012 |
| ES | 465719 | 12/1980 |
| FI | 773650 | 6/1978 |
| FR | 2374886 | 7/1978 |
| GB | 1550577 | 8/1979 |
| IT | 1081824 | 5/1985 |
| JP | S5613462 | 7/1978 |
| JP | 2006512954 | 4/2006 |
| JP | 4481173 | 6/2010 |
| JP | 5380789 | 1/2014 |
| JP | 5826771 | 12/2015 |
| NL | 7713563 | 6/1978 |
| NO | 774411 | 6/1978 |
| WO | WO08504903 | 11/1985 |
| WO | WO9107116 | 5/1991 |
| WO | WO0215799 | 7/2002 |
| WO | WO2004062863 | 7/2004 |
| WO | WO2007008703 | 1/2007 |
| WO | WO2009151926 | 12/2009 |
| WO | WO2011100313 | 8/2011 |
| WO | WO2012166476 | 12/2012 |
| WO | WO2014150514 | 9/2014 |
| WO | WO2015006296 | 1/2015 |
| WO | WO2015166487 | 11/2015 |

* cited by examiner

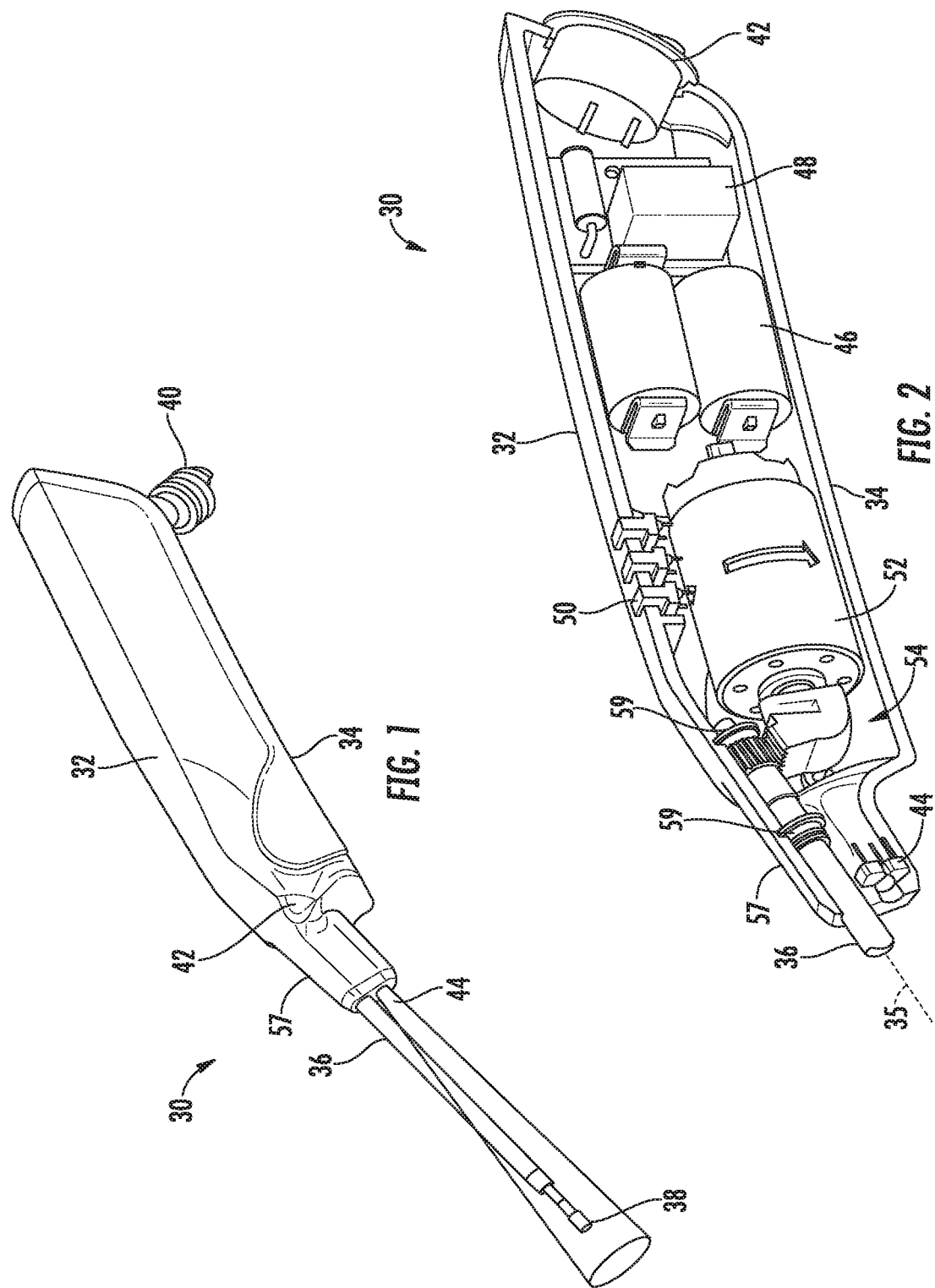

ROTARY OSCILLATING SURGICAL TOOL

PRIORITY CLAIM

In accordance with 37 C.F.R. 1.76, a claim of priority is included in an Application Data Sheet filed concurrently herewith. Accordingly, the present invention claims priority to U.S. Provisional Patent Application No. 62/423,624, entitled "ROTARY OSCILLATING SURGICAL TOOL", filed Nov. 17, 2016. The contents of the above referenced application are incorporated herein by reference.

FIELD OF THE INVENTION

The present invention relates to an oscillating rotary tool with a cutter adapted to modify tissue such as bone, cartilage and discs.

BACKGROUND OF THE INVENTION

The prior art has provided surgical tools having a rotary cutter adapted to modify tissue such as bone, cartilage and discs in a patient. Such tools, though, present a problem if the cutter encounters fibrous tissue such as muscle and nerves. Such fibrous tissue can wrap around the cutter and be damaged thereby. The prior art has also provided oscillating rotary tools for such surgical procedures, but the mechanisms used to effect oscillation of the cutter during its rotation do not operate smoothly due to the mechanism used to effect oscillation. An advance in such oscillating tools is represented by our co-pending application Ser. No. 13/469,665, filed May 11, 2012, in the name of Peter L. Bono.

SUMMARY OF THE INVENTION

According to one embodiment of the present invention, a surgical tool is provided with a housing, a cutter support shaft is operably connected to a motor to effect rotation of the shaft, with a drive transmission configured between the motor and the shaft to effect oscillating rotary movement of the shaft and cutter.

It is thus an objective of the present invention to provide an oscillation effecting drive transmission that utilizes a planetary gear set operably connected to the motor with the ring gear of said planetary gear set being fixed against rotation.

It is another objective of the present invention to provide an oscillation effecting drive transmission that utilizes the pinion gear of the planetary gear set that is coupled to the motor via an input crank such that the pinion gear revolves about the axis of rotation of the motor output shaft positioned inside the ring gear.

It is yet another objective of the present invention to provide an oscillation effecting drive transmission whereby the planetary gear set and input crank are operably coupled to an output driver connected to the pinion gear of the planetary gear set with a portion of the pinion gear having a motion path that is substantially linear, forming a Cardan mechanism.

Still yet another objective of the present invention is to provide a Cardan mechanism operably coupled to the cutter shaft via a motion translation mechanism which includes the output driver coupled to a pivotally mounted follower having a sector gear operable to engage a second pinion gear connected to the shaft that drives the cutter.

Other objects and advantages of this invention will become apparent from the following description taken in conjunction with any accompanying drawings wherein are set forth, by way of illustration and example, certain embodiments of this invention. Any drawings contained herein constitute a part of this specification, include exemplary embodiments of the present invention, and illustrate various objects and features thereof.

BRIEF DESCRIPTION OF THE FIGURES

FIG. 1 is a perspective view of the surgical tissue removal tool;

FIG. 2 is a cutaway perspective view of the surgical tool of FIG. 1;

DETAILED DESCRIPTION OF THE INVENTION

Figure 3:
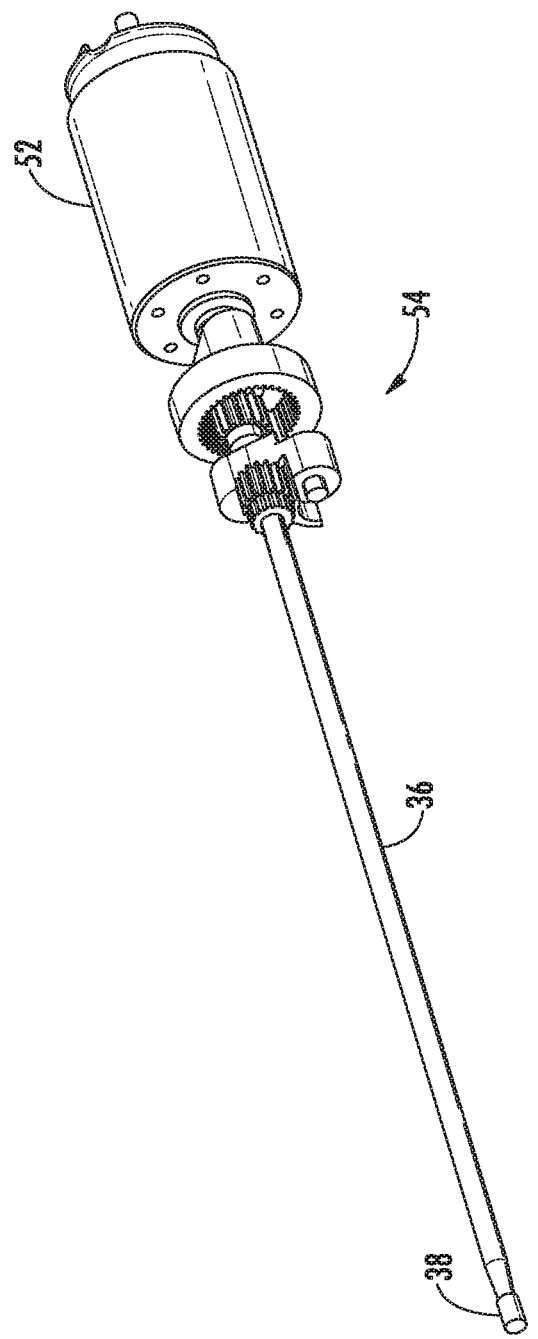
FIG. 3 is a fragmentary perspective view showing details of the internal parts of the surgical tool shown in FIG. 1.

The reference numeral 30 designates generally a rotary oscillating surgical tool useful particularly in the modification or removal of hard tissue such as bone, cartilage and disc tissue. The surgical tool 30 is a handheld tool with a housing 32 providing a handle 34 for manually gripping the tool 30 for use during a surgical procedure. While one shape and style of handle 34 is illustrated, any suitable shape and style of handle can be provided. For example, a right angle pistol grip may be added. Additionally, the housing may have a narrow front portion for a smaller pencil-like "precision grip", while the larger remaining portion is sized to balance in the user's hand, such as in the web area between the index finger and thumb for allowing better control with less fatigue.

The tool 30 can be used in surgical operations, such as spinal surgery, wherein tissue such as bone, cartilage and disc material that is preferably of a non-fibrous tissue type may be modified or removed, such as from the spine of a patient. The tool 30 has an output shaft 36, which is driven to rotate in an oscillating manner of two alternate directions about the longitudinal axis 35 of the shaft 36. Shaft 36 is provided with a cutting tool or cutter 38 positioned and secured to a distal end portion of the shaft 36. The cutter 38 is driven to rotate in alternate directions, like the shaft 36, with a limited range of angular displacement of rotation. It has been found that such oscillatory rotation is effective in cutting or modifying hard tissue like bone, cartilage and portions of discs. It has also been found that this oscillatory rotation reduces the risk of damage to fibrous tissue like muscle and nerve.

The tool 30 can receive energy for its operations from an external supply, such as a direct current power supply cord 40. A power control switch 42 may be provided on the housing 32 for controlling the operation of the tool 30, such as in an on and off manner and/or in a variable rotational speed manner. A light source 44 may also be provided on the housing 32 for illuminating the surgical site. Such a light source may be a light emitting diode (LED) which can be powered directly or indirectly by energy from the cord 40.

FIG. 2 illustrates the internal components of the tool 30. An energy source may be provided by a battery supply 46 mounted in the housing 32. The battery supply 46 may be charged by the power cord 40. Electronics 48 are provided in the housing 32 for controlling the operation of the tool 30. The power switch 42 may alternatively be located at the distal end of the housing as opposed to the illustrated position at the intermediate section of the housing 32. A plurality of indicator lamps 50 may also be provided on the housing 32, and can be LEDs for indicating operational characteristics of the tool 30, such as the state of charge of the battery supply 46. Alternately, the batteries 46 can be eliminated in favor of the cord 40 being connected to a source of electrical energy. Additionally, the motor 52 can be powered by compressed air, a vacuum or any other suitable source of energy that would, on demand, effect rotation of a rotor portion of the motor 52.

The motor 52 is suitably mounted in the housing 32, wherein a portion of the motor, a rotor, is free to rotate and ultimately drive the shaft 36. A portion of the motor 52 is fixed against rotation in the housing 32 as is known in the art, for example, a motor housing and/or stator. The motor 52 drives the shaft 36 through a transmission 54 that is operable for converting continuous rotary motion from the motor 52 to rotary oscillation to the shaft 36. The shaft 36 is suitably mounted in the nose 57 of the housing 32 as in bearings 59. The shaft 36 may be angled relative to the longitudinal axis of the housing 32, as depicted in FIG. 2, for ergonomics. Cooling fins or a cooling fan, not shown, may be attached to or near the motor 52 for cooling the motor and/or the tool 30.

The transmission 54, as best seen in FIGS. 3-9, is positioned in the housing 32 and operably couples the shaft 36 to the motor 52, and is operable to convert the continuous rotary motion of the output shaft 60 of the motor 52 to oscillating rotary motion of the shaft 36. By oscillating rotary motion, it is meant that the shaft 36 will rotate a portion of a complete revolution, first in one rotation direction then in another rotation direction, say first counterclockwise, then clockwise, then counterclockwise again and so on. To effect this movement, the transmission 54 comprises two sections. The first section is designated generally 61 and is operable to convert the rotary motion of the shaft 60 of the motor 52 to reciprocating generally linear motion of a portion thereof, and the second section is designated generally 62 and is operable to convert that reciprocating generally linear motion to oscillating rotary motion.

Figure 4:
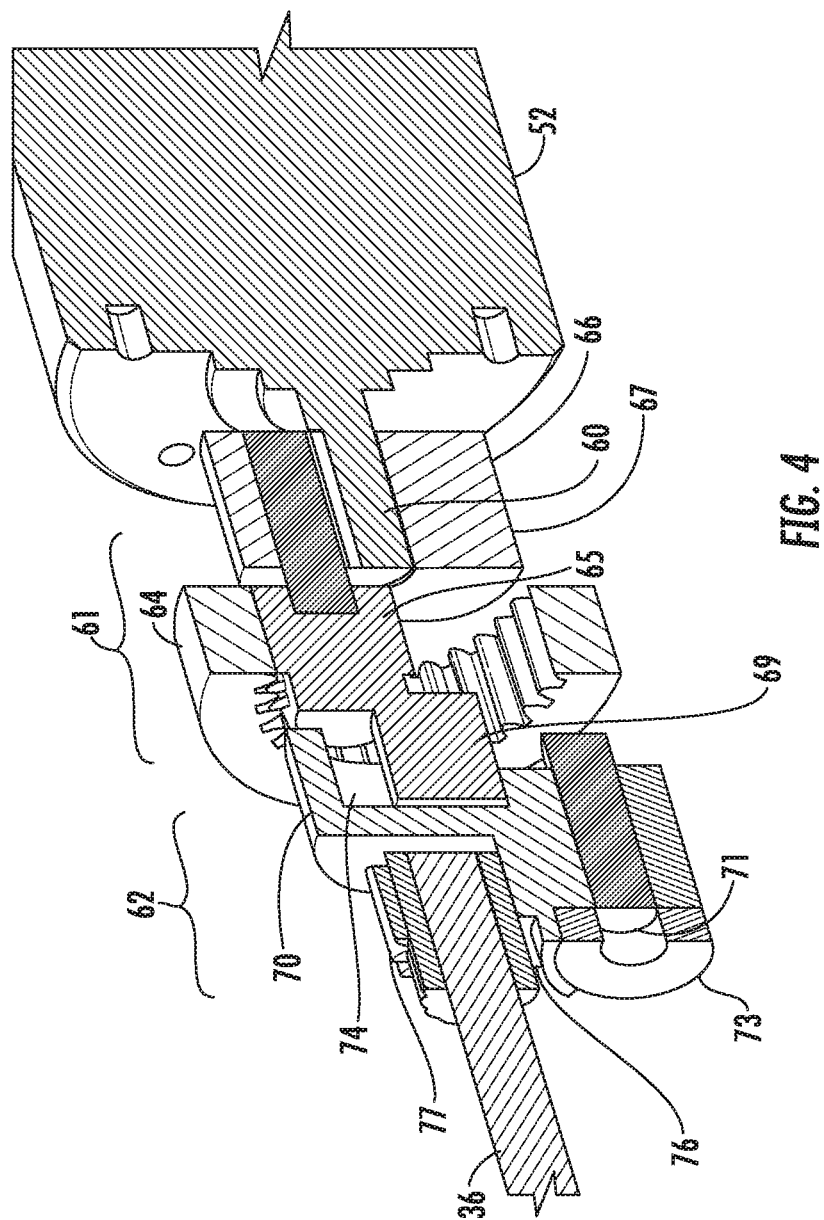
FIG. 4 is an enlarged fragmentary perspective view of a transmission portion of the surgical tool of FIG. 1 with portions broken away to show details.
Figure 5:
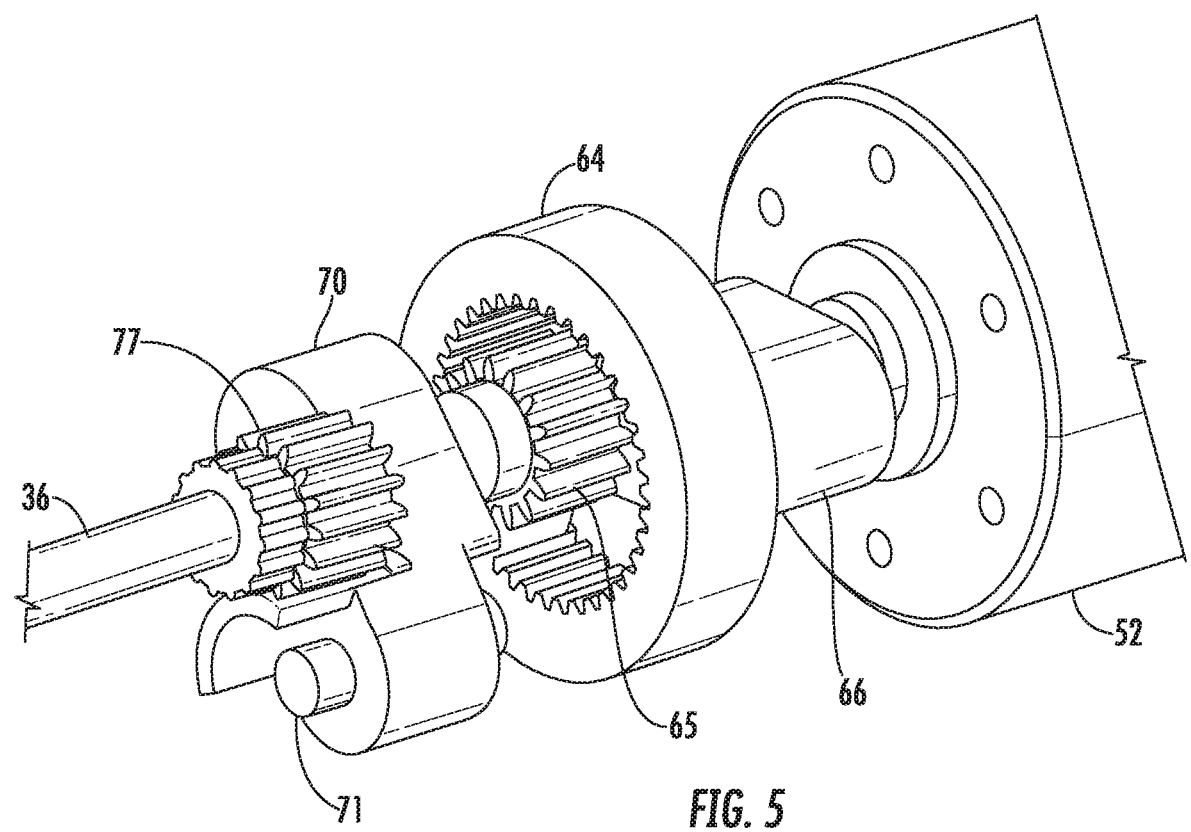
FIG. 5 is a figure similar to FIG. 4 showing portions of the transmission in a first rotational position.
Figure 6:
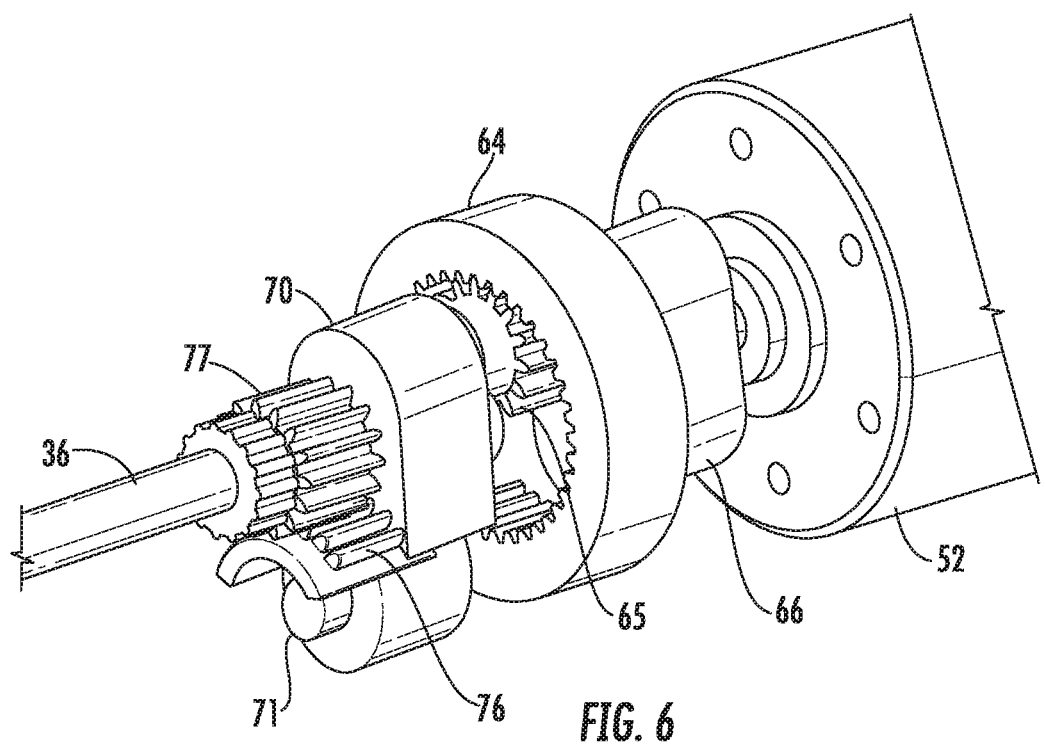
FIG. 6 is a figure similar to FIG. 5 showing portions of the transmission in a second rotational position.
Figure 7:
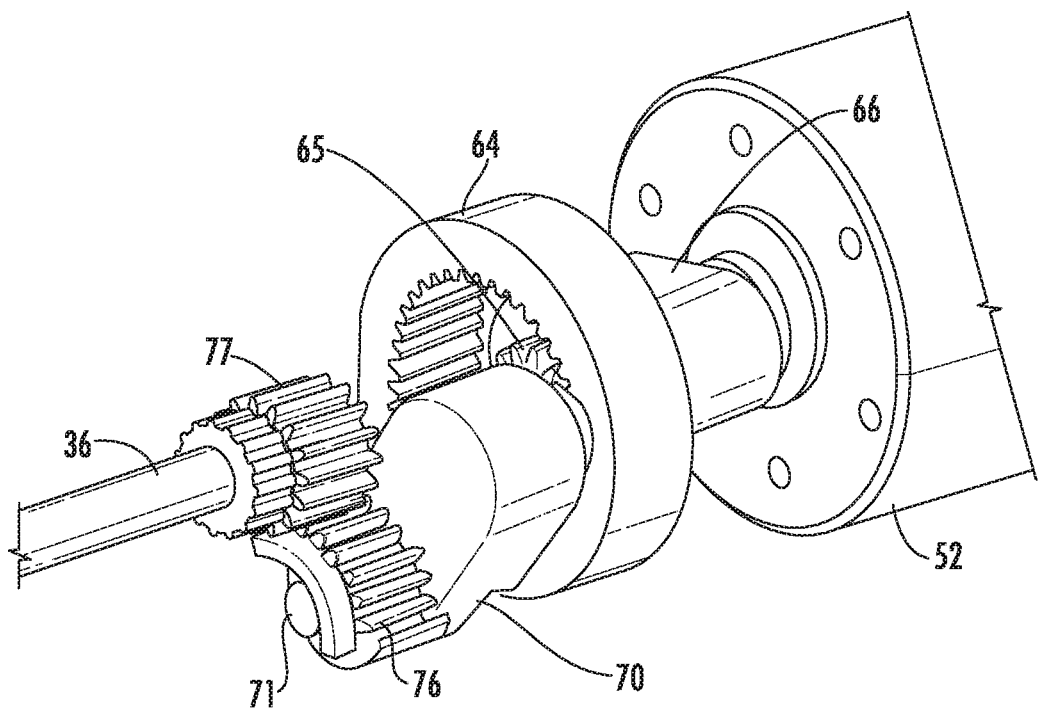
FIG. 7 is a figure similar to FIG. 4 showing portions of the transmission in a third rotational position.
Figure 8:
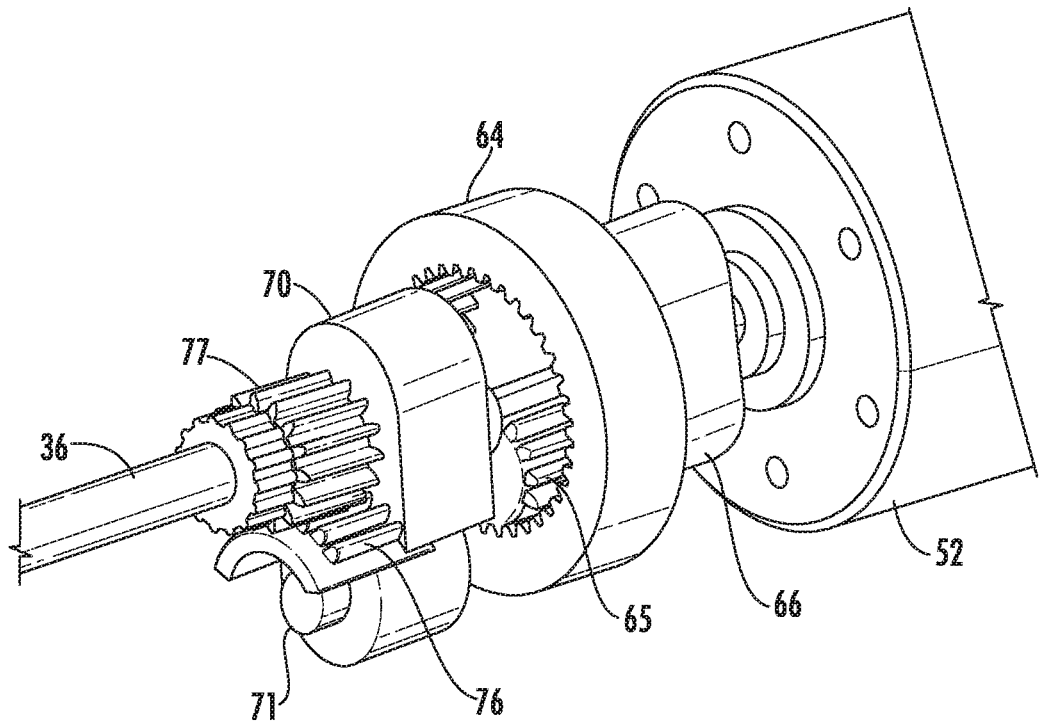
FIG. 8 is a figure similar to FIG. 4 showing portions of the transmission in a fourth rotational position.
Figure 9:
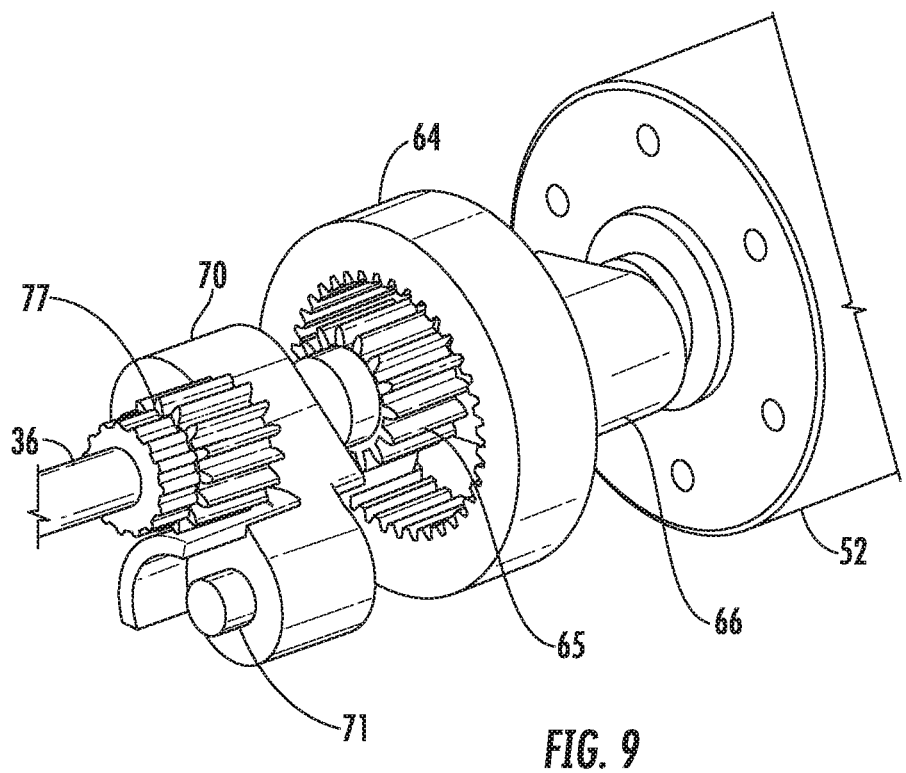
FIG. 9 is a figure similar to FIG. 4 showing portions of the transmission in a fifth rotational position.

In the illustrated embodiment, the transmission section 61 is in the form of a Cardan mechanism that utilizes an internal toothed ring gear 64 and an external toothed pinion gear 65, with the pinion gear 65 being positioned inside of and having its external gear teeth in engagement with the internal gear teeth of the ring gear 64. The gear ratio of the ring gear 64 to pinion gear 65 is 2:1. The ring gear 64 is suitably fixed in the housing 32 to prevent its motion relative to the housing 32. The pinion gear 65 is suitably mounted to a crank arm 66, which in turn is secured to the shaft 60 of the motor 52 and is offset from the axis of rotation of the shaft 60, whereby the pinion gear 65 revolves about the axis of rotation of the shaft 60 while inside the ring gear 64. Preferably, the crank arm 66 has a counterweight 67 opposite of where the pinion gear 65 is mounted to the crank arm 66. In a Cardan mechanism, one point on the pinion gear will move generally linearly in a reciprocating manner within the ring gear associated therewith. In the illustrated embodiment, as oriented as seen in FIG. 4, the path of movement of this point is timed to move in a generally transverse plane relative to a portion of the first section 61 of the transmission 54. Secured to the pinion gear 65, preferably in an integral manner, is a driver arm 69 that extends forwardly of the ring gear 64 for receipt in a follower 70 to effect movement of the follower 70 in response to movement of the arm 69. The follower 70 is suitably mounted in the housing 32 in a manner to permit its pivoting movement about an axle 71. The transverse linear movement of a spot on the pinion gear 65 is generally transverse to the longitudinal axis of elongate slot 74 in the follower 70. The axle 71 is suitably mounted in bearing supports 73 that are in turn suitably mounted to the housing 32. While only one bearing support 73 as shown, it is preferred that each end of the axle 71 have a bearing 73 associated therewith. It is to be understood that the axle 71 could utilize the follower 70 as a bearing for rotation of the follower 70 about the axle 71, and have the axle 71 mounted to the housing 32 in a fixed manner. The driver arm 69 is received within the elongate slot 74 for effecting movement of the follower 70 in a rotary oscillating manner. The follower 70 moves in an oscillating rotary manner about the axis of the axle 71. When a portion of the driver arm 69 is moving in its linear path, portions of the arm 69 engage sides of the slot 74 to effect movement of the follower 70 in response to movement of the driver arm 69. This movement can be seen in various orientations illustrated in FIGS. 5-9. In the illustrated structure, the driver 69 is offset to the outside of the outside diameter of the pinion gear 65, and thus its central axis does not move in a linear path, but will move in a series of arcs that are elongated in a horizontal plane and reduced in the vertical direction as seen in the orientation of the tool 30 in FIG. 2. This back-and-forth and up-and-down movement is accommodated by constructing the slot 74 to be elongated, as best seen in FIG. 4. As the driver 69 moves in its path, it affects oscillating rotary motion of the follower 70 about the axle 71. Two counter-clockwise and two clockwise oscillations of the cutter 38 are effected, and four oval paths by a portion of the driver 69 are traversed for each revolution of the pinion gear 65 within the ring gear 64. The follower 70 is provided with a drive gear, such as a sector gear 76, that is operably coupled to a driven gear member 77 secured to the shaft 36. As the follower 70 moves, the shaft 36 moves in response thereto by engagement between the gears 76 and 77. Because the follower 70 moves in a rotary oscillating manner, the shaft 36 also moves in a rotary oscillating manner. The components of the transmission sections 61, 62 are configured relative to one another such that, when the rotary oscillating movement changes direction at the shaft 36, the applied torque by the motor 52 would be high; while at the center of one oscillation, the applied torque by the motor 52 would be lower. This assists in providing a high starting torque for the cutter 38 to reverse rotation direction.

All patents and publications mentioned in this specification are indicative of the levels of those skilled in the art to which the invention pertains. All patents and publications are herein incorporated by reference to the same extent as if each individual publication was specifically and individually indicated to be incorporated by reference.

It is to be understood that while a certain form of the invention is illustrated, it is not to be limited to the specific form or arrangement herein described and shown. It will be apparent to those skilled in the art that various changes may be made without departing from the scope of the invention and the invention is not to be considered limited to what is shown and described in the specification and any drawings/figures included herein.

One skilled in the art will readily appreciate that the present invention is well adapted to carry out the objectives and obtain the ends and advantages mentioned, as well as those inherent therein. The embodiments, methods, procedures and techniques described herein are presently representative of the preferred embodiments, are intended to be exemplary, and are not intended as limitations on the scope. Changes therein and other uses will occur to those skilled in the art which are encompassed within the spirit of the invention and are defined by the scope of the appended claims. Although the invention has been described in connection with specific preferred embodiments, it should be understood that the invention as claimed should not be unduly limited to such specific embodiments. Indeed, various modifications of the described modes for carrying out the invention which are obvious to those skilled in the art are intended to be within the scope of the following claims.

What is claimed is:

1. An oscillating rotary surgical tool including;
a housing forming a handle;
a motor mounted in the housing, said motor having a rotary output first shaft;
a second shaft rotatably carried by the housing and having a cutter positioned at a distal end of the shaft;
a transmission mounted in the housing and operably associated with the motor and coupling the first shaft to the second shaft, said transmission having a first section and a second section with the first section including a planetary gear set, said planetary gear set including a ring gear fixed against rotation relative to the housing and including a first pinion gear coupled to the motor to effect its movement within the ring gear revolving about the first shaft, said first section also including a driver mounted to the first pinion gear and movable therewith, said second section including a follower operably associated with the driver, said follower being pivotally mounted in the housing and movable in an oscillating manner in response to movement of the driver effected by rotation of the first shaft, said follower including a drive gear also movable in a rotary oscillating manner, said drive gear being in engagement with a driven gear member secured to said second shaft, whereby said second shaft is moved in a rotary oscillating manner by rotation of the first shaft.

2. The surgical tool of claim 1 wherein the gear ratio of the ring gear to the first pinion gear being 2:1.

3. The surgical tool of claim 2 wherein the first pinion gear being coupled to the first shaft with a crank arm.

4. The surgical tool of claim 3 wherein the follower is operable for movement in reciprocal rotary oscillation about an axle on which it is pivotally mounted.

5. The surgical tool of claim 4 wherein the follower including an elongate slot with a portion of the driver received therein.

6. The surgical tool of claim 4 wherein the drive gear being a sector gear moveable in an arc about the axle in reciprocal rotary oscillation.

7. The surgical tool of claim 6 wherein the second shaft having the driven gear member secured thereto and coupled to the sector gear, whereby reciprocal rotary oscillation of the sector gear effects reciprocal rotary oscillation of the driven gear member and the second shaft.

8. The surgical tool of claim 7 wherein the second shaft including the cutter on a distal end thereof and movable in reciprocal rotary oscillation with the second shaft.

9. The surgical tool of claim 8 wherein the motor being an electric motor.

10. The surgical tool of claim 9 including a power source carried in the housing, said power source including at least one battery.

* * * * *